(12) United States Patent
Flanagan et al.

(10) Patent No.: US 8,550,089 B2
(45) Date of Patent: Oct. 8, 2013

(54) MAGNETIC PARTICLES FOR DELIVERING THERAPEUTIC AGENT TO A TARGET LOCATION

(75) Inventors: Aiden Flanagan, Galway (IE); Kent Harrison, Maple Grove, MN (US); Liliana Atanasoska, Edina, MN (US); David J. Sogard, Edina, MN (US); Liza J. Davis, St. Michael, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 313 days.

(21) Appl. No.: 12/765,369

(22) Filed: Apr. 22, 2010

(65) Prior Publication Data

US 2010/0269838 A1 Oct. 28, 2010

Related U.S. Application Data

(60) Provisional application No. 61/173,432, filed on Apr. 28, 2009.

(51) Int. Cl.
*A61B 19/00* (2006.01)

(52) U.S. Cl.
USPC .......................................................... 128/897

(58) Field of Classification Search
USPC .............. 600/9; 128/897, 899; 424/1.11, 9.52
See application file for complete search history.

(56) References Cited

U.S. PATENT DOCUMENTS

| 4,247,406 A | 1/1981 | Widder et al. |
| 7,218,962 B2 | 5/2007 | Freyman |
| 2006/0009674 A1* | 1/2006 | Miller .............................. 600/30 |
| 2006/0057211 A1 | 3/2006 | Chorny et al. |
| 2008/0006281 A1* | 1/2008 | Sih et al. ............................ 600/9 |
| 2009/0082611 A1* | 3/2009 | Levy et al. ......................... 600/9 |

FOREIGN PATENT DOCUMENTS

| GB | 2 415 374 A | 12/2005 |
| JP | 56-51411 A | 5/1981 |
| WO | 02/24248 A1 | 3/2002 |

OTHER PUBLICATIONS

International Search Report and Written Opinion from related International Application No. PCT/US2010/032035, mailed Jul. 15, 2011.
Pankhurst, Q.A., et al., "Applications of magnetic nanoparticles in biomedicine," Journal of Physics D: Applied Physics, vol. 36, No. 13 (Jun. 18, 2003), pp. R167-R181, IOP Publishing, Bristol, GB.
Leonard A. Levin, MD, PhD, et al., "History of Neuroprotection and Rationale as a Therapy for Glaucoma," The American Journal of Managed Care, vol. 14, No. 1, pp. S11-S14, Feb. 2008.

* cited by examiner

*Primary Examiner* — Christine Matthews
(74) *Attorney, Agent, or Firm* — Kenyon & Kenyon LLP

(57) ABSTRACT

A system for delivering therapeutic agent to a target location in a body in accordance with one embodiment is provided comprising a plurality of magnetic particles, each magnetic particle carrying a therapeutic agent, and a magnetic device for attracting the magnetic particles to a target location. The magnetic particles may be delivered by a catheter into a blood vessel upstream from the target location so that they travel toward the target location. A method for delivering therapeutic agent to a target location in a body in accordance with another embodiment comprises providing a plurality of magnetic particles, each magnetic particle carrying a therapeutic agent, placing a magnetic device in a position to attract the magnetic particles to a target location, and allowing the magnetic particles to infuse the target location by the attraction of the magnetic particles to the magnetic device. The therapeutic agent may comprises a therapeutic agent for preventing or treating reperfusion injury, and the step of providing the plurality of magnetic particles may comprise delivering the plurality of magnetic particles through a blood vessel.

13 Claims, 2 Drawing Sheets

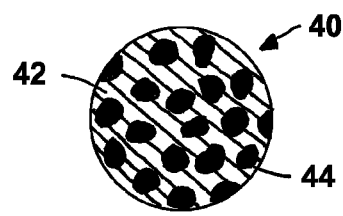 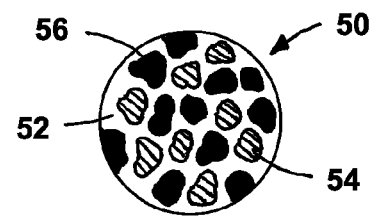
FIG. 4　　　　　FIG. 5
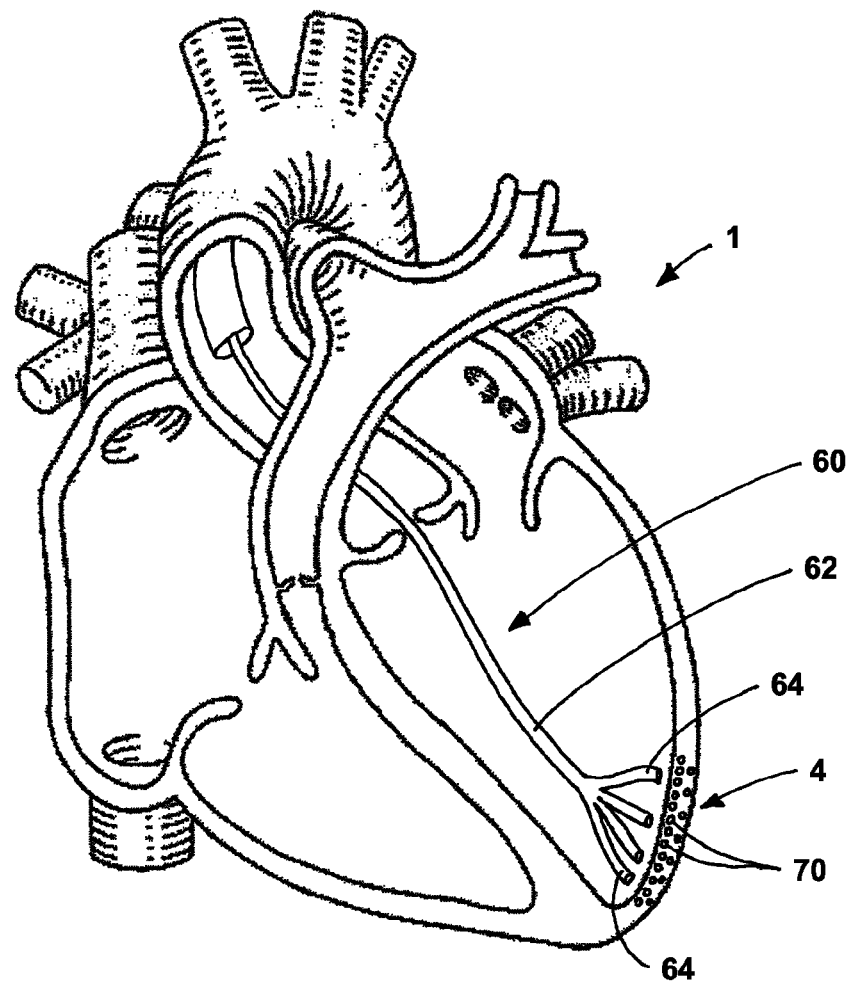
FIG. 6

MAGNETIC PARTICLES FOR DELIVERING THERAPEUTIC AGENT TO A TARGET LOCATION

CROSS REFERENCE TO RELATED APPLICATION

The present application claims priority to U.S. provisional application Ser. No. 61/173,432 filed Apr. 28, 2009, the disclosure of which is incorporated herein by reference in its entirety.

TECHNICAL FIELD

The present invention relates to medical devices and methods for delivering therapeutic agent to a target location in a body.

BACKGROUND

Blockage of arteries, such as the coronary arteries, can result in reduced blood flow to the downstream tissue, such as the heart muscle. In the case of the coronary arteries, such a blockage can lead to acute myocardial infarction or heart attack. Various treatments have been proposed to restore blood flow to the affected area, e.g., the ischemic myocardium. This process of restoring blood flow to the affected area is known as reperfusion.

Treatments that have been proposed to restore blood flow include thrombolytic therapy, percutaneous coronary intervention (PCI) and bypass surgery. Thrombolytic therapy involves the administration of therapeutic agents to open the blockage. Some thrombolytic agents that have been proposed or used include streptokinase, urokinase, and alteplase (recombinant tissue plasminogen activator, rtPA).

Percutaneous coronary intervention involves delivering a treatment device to the affected area of the blood vessel to open the blocked site. Commonly, an angioplasty procedure is performed in which a balloon catheter is tracked through the vasculature, and, once the balloon is at the constriction, the balloon is expanded to open the blockage. Often a stent is expanded and left at the site to help maintain the patency of the vessel.

Coronary artery bypass surgery involves a graft vessel being taken from the patient and implanted to bypass the area of blockage. Blood then is allowed to flow around the blockage through the bypass graft.

Reperfusion of blood flow to the ischemic tissue, while beneficial, can at times result in damage to the tissue. Because the affected tissue has been deprived of oxygen and nutrients, the restoration of blood flow can result in inflammation and oxidative damage. This is known as reperfusion injury.

Some techniques have been proposed to prevent and/or treat reperfusion injury. For example, glisodin has been proposed as a therapeutic treatment. However, there continues to be a need for improved techniques to prevent and/or treat reperfusion injury.

In addition to the foregoing, there is also a need for improved techniques for delivering therapeutic agent to a target location in a body. For example, there is a need for improved techniques for delivering therapeutic agent to prevent and/or treat reperfusion injury. As another example, there is a need for improved techniques for delivering therapeutic agent to tumors, e.g., for chemotherapy, particularly to hard to reach tumors. As another example, there is a need for improved techniques for delivering therapeutic agent for localized neuroprotection, such for delivering therapeutic agent to retinal ganglion cells for the prevention of glaucoma progression.

SUMMARY

In one embodiment, the present invention provides a system for delivering therapeutic agent to a target location in a body comprising a plurality of magnetic particles, each magnetic particle carrying a therapeutic agent, and a magnetic device for attracting the magnetic particles to a target location. The system may further comprise a catheter for delivering the magnetic particles into a blood vessel upstream from the target location. The therapeutic agent may comprise a therapeutic agent for preventing or treating reperfusion injury, and the target location may comprise myocardial tissue.

The magnetic particles may take various forms. A magnetic particle may comprise a magnetic core and a coating in which the therapeutic agent is contained. A magnetic particle may comprise a core in which the therapeutic agent is contained and a coating comprising magnetic material. A magnetic particle may comprise a porous magnetic material loaded with therapeutic agent. A magnetic particle may comprise a matrix carrying magnetic material and the therapeutic agent.

In another embodiment, the present invention provides a method of delivering therapeutic agent to a target location in a body comprising providing a plurality of magnetic particles, each magnetic particle carrying a therapeutic agent, placing a magnetic device in a position to attract the magnetic particles to a target location, and allowing the magnetic particles to infuse the target location by the attraction of the magnetic particles to the magnetic device. The therapeutic agent may comprises a therapeutic agent for preventing or treating reperfusion injury, and the step of providing the plurality of magnetic particles may comprise delivering the plurality of magnetic particles through a blood vessel. The step of delivering the plurality of magnetic particles through a blood vessel may be performed simultaneously or nearly simultaneously with a reperfusion procedure.

BRIEF DESCRIPTION OF THE DRAWINGS

FIG. 4 shows a magnetic particle in accordance with another embodiment of the invention.

FIG. 5 shows a magnetic particle in accordance with another embodiment of the invention.

FIG. 6 shows the inside of a heart with a magnetic device placed endocardially in accordance with an embodiment of the invention.

DETAILED DESCRIPTION

Figure 1:
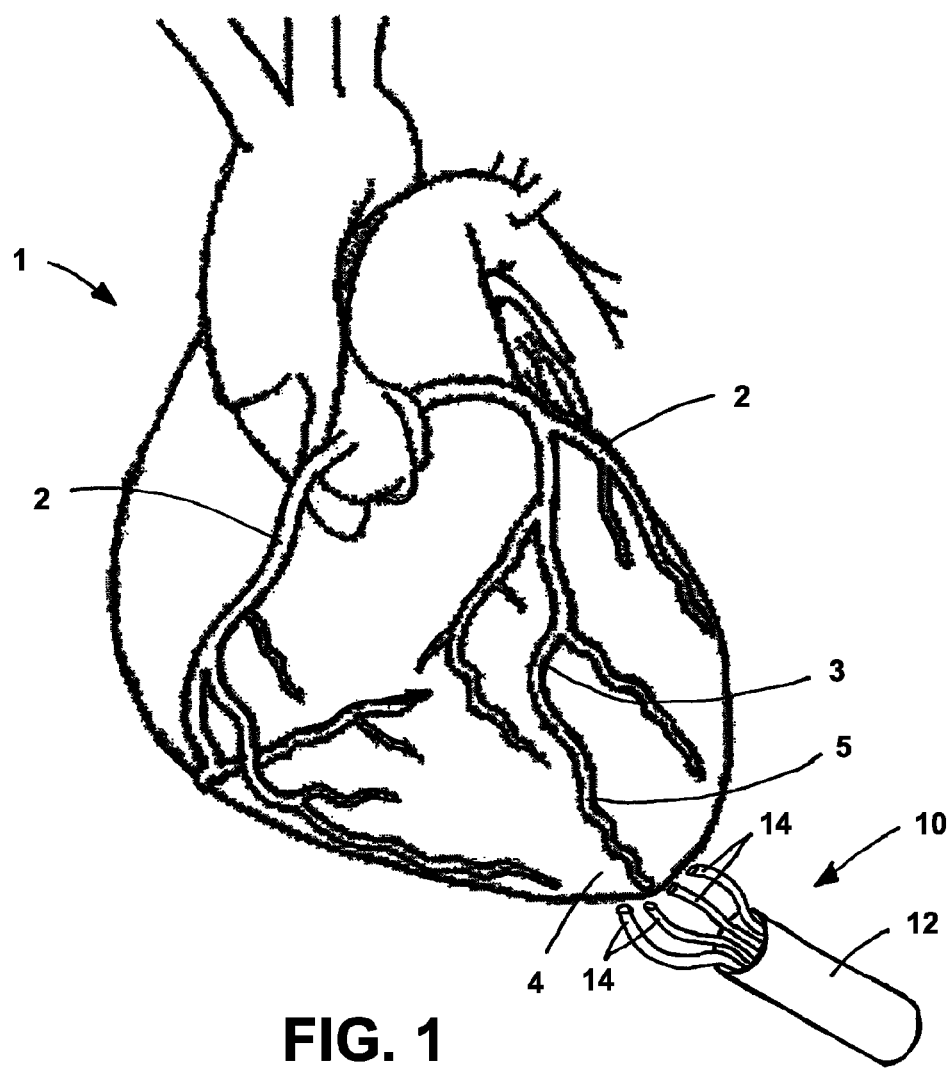
FIG. 1 shows the outside of a heart with a magnetic device placed epicardially in accordance with an embodiment of the invention.

FIG. 1 shows the outside of a heart 1 with epicardial coronary arteries 2 visible. In the event of a coronary artery blockage, for example at area 3 in FIG. 1, blood flow is restricted or cut off to downstream tissue, for example affected tissue area 4, i.e., ischemic myocardium 4, in FIG. 1.

Reperfusion can be achieved by various methods known in the art, such as thrombolytic therapy, percutaneous coronary intervention (PCI) such as angioplasty, stenting, and/or ablation, and bypass surgery. When reperfusion occurs, blood flow is restored to the ischemic myocardium 4.

Figure 2:
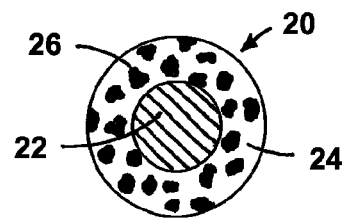
FIG. 2 shows a magnetic particle in accordance with an embodiment of the invention.

FIG. 2 shows a magnetic particle 20 in accordance with an embodiment of the invention to help prevent and/or treat reperfusion injury when blood flow is restored to the ischemic tissue. The magnetic particle in this embodiment is a nanoparticle having a ferromagnetic core 22 and a coating 24 in which a therapeutic agent 26 is contained. The therapeutic agent 26 can be one or more drugs that, when released at the site of the ischemic tissue to which blood flow is restored, will help prevent and/or treat reperfusion injury.

Magnetic particles with therapeutic agent such as that shown in FIG. 2 can be used in conjunction with one or more magnetic devices such as those FIG. 1 and FIG. 6 (described below) for attracting the magnetic particles to the ischemic tissue. FIG. 1 shows a magnetic device 10 that includes an elongated member 12 and a series of magnetic elements 14.

In accordance with certain embodiments of the invention, a technique is provided in which particles that are magnetic and that contain therapeutic agent, such as the magnetic particles 20, are delivered and drawn by magnetism to a specific target area. For example, nanoparticles 20 are released into the artery 5 during angioplasty of the obstructed area 3. This may be accomplished, for example, through a perfusion lumen of an angioplasty catheter, by a separate infusion catheter, or by any other suitable mechanism. The infusion of the magnetic particles can be done simultaneously with the angioplasty procedure or nearly simultaneously with the angioplasty procedure.

In accordance with this example procedure, the magnetic device 10 is placed as shown in FIG. 1, with the magnetic elements 14 positioned epicardially as shown in FIG. 1. Because the nanoparticles 20 have magnetic cores 22, they are attracted by the magnetic elements 14 to the area of the ischemic myocardium 4 which is prone to reperfusion injury. In this way, the therapeutic agent 26 is delivered in a targeted way to the affected area. The magnetic device generally keeps the magnetic particles in the target area, preventing them from diffusing away from the target tissue through the vasculature. In this way, the therapeutic agent is mostly released into the affected or infarct region, where it prevents or treats reperfusion injury.

The particles that are used in accordance with the invention can be sized in a manner to facilitate infusion into the affected tissue. The particles can diffuse through the vessel wall and into the tissue and can be taken up into the tissue easily. In certain embodiments, the particles are on a nanometer scale, for example around 200 nm or less for cardiac applications. Other sizes are possible, including, for example, particles on a micrometer scale, for example around 50 μm.

The magnetic device may be any suitable magnetic mechanism for attracting the magnetic particles to the desired location. For example, the magnets on the end of the catheter magnetic elements may be made of any suitable magnetic material, for example very strong magnets such as rare earth magnets like neodymium-iron-boron. The magnets can also electromagnets. The magnetic elements can be, for example, strands that are magnetized on their ends and/or wires capable of carrying a current for electromagnets on the ends of the strands. Alternatively, the magnetic device may have a single magnetic element. Other embodiments are of course possible.

In certain embodiments, the magnetic field generated by the magnetic device can be alternated in order to agitate the magnetic particles and encourage permeation into the tissue. The alternation can be achieved by changing the current in an electromagnet or by moving permanent magnets back and forth.

The magnetic material of the magnetic particles can be any suitable magnetic material capable of being attracted by the magnetic device such that the magnetic particles are drawn to the target area. For example, suitable materials include those strongly attracted by a magnetic field, i.e. ferromagnets: iron, nickel, cobalt, nickel-iron, nickel-zinc-iron, FeO (magnetite), and rare earth magnet alloys like neodymium-iron-boron.

The therapeutic agent in the magnetic particles can be any of a number of therapeutic agents suitable for preventing and/or treating (e.g., alleviating) reperfusion injury. The therapeutic agents may include, for example, anti-inflammatory agents, free radical scavengers, and/or vasodilators, as are known in the art.

In the embodiment of FIG. 2, the magnetic particle has a ferromagnetic core and a coating with a therapeutic agent. The coating may be, for example, a polymer coating in which the therapeutic agent is carried. Upon delivery, the therapeutic agent can elute from the polymer coating into the target tissue. The polymer in certain embodiments can be a biodegradable polymer.

Figure 3:
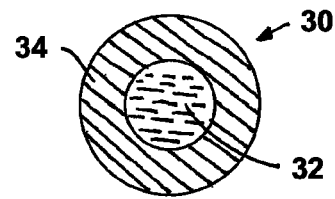
FIG. 3 shows a magnetic particle in accordance with another embodiment of the invention.

FIG. 3 shows a magnetic particle in accordance with another embodiment of the invention. The magnetic particle in this embodiment is a nanoparticle 30 having a core 32 in which a therapeutic agent is contained. The core 32 may be, for example, a liquid or solid core. Outside of the core 32, the nanoparticle 30 has a coating 34 formed of or containing a magnetic material. The coating 34 may be, for example, porous, to allow therapeutic agent to diffuse from the core 32 through the coating 34 to the affected tissue at the target area.

The magnetic particles may be formed in any of a number of suitable ways. For example, magnetic particles having a magnetic core and outer coating can be formed by dip coating magnetic particles in a mixture of polymer, therapeutic agent and solvent. When the solvent evaporates or is driven off, the magnetic particle is left with a polymer coating containing the therapeutic agent. As another example, magnetic particles can be spray coated with a mixture of polymer, therapeutic agent and solvent, after which the solvent evaporates or is driven off. Magnetic particles having a porous magnetic coating and inner core can be made by coating a removable material, such as a meltable material, with a porous magnetic coating, and then removing the removable material, e.g., by melting it and allowing it to diffuse through the porous outer coating. Then, the porous outer coating can be filled with the therapeutic agent by dipping or by any other suitable method. In order to facilitate the loading of the therapeutic agent into the porous shells, the porous shells may be loaded into a vacuum chamber which evacuates the internal volume. Then the chamber is flushed with the therapeutic agent and the pressure is elevated to force the therapeutic agent through the pores and into the magnetic particle. As another example, a solid core containing therapeutic agent can be coated with a porous magnetic shell by nanoparticle bombardment. Equipment for such a technique can obtained from or adapted from that obtained from Mantis Deposition Ltd.

As an alternative to the magnetic particles shown in FIGS. 2 and 3, and particle may be formed in which there is no distinct core but rather a continuous porous magnetic material loaded with therapeutic agent. An example of such a particle is shown in FIG. 4. FIG. 4 shows a magnetic particle 40 comprising a porous magnetic material 42 in which therapeutic agent 44 is loaded in the pores. Such particles can be made by first forming the porous particles and then loading them with therapeutic agent as described above. For example, the porous particles can be filled with therapeutic agent by dipping or by any other suitable method. The porous particles may be loaded into a vacuum chamber which evacuates the pores, and then the chamber can be flushed with the therapeutic agent and the pressure elevated to force the therapeutic agent through the pores and into the magnetic particle.

As another alternative magnetic particle, a particle may be formed with a matrix in which magnetic material is carried as particles and in which therapeutic agent is also carried. An example of such a particle is shown in FIG. 5. FIG. 5 shows a magnetic particle 50 comprising a matrix 52, such as a polymer matrix, carrying magnetic material 54 as particles as illustrated. Therapeutic agent 56 is also carried in the matrix. Such particles 50 can be made in various ways. For example, the polymer can be dissolved in a solvent and then the magnetic material and therapeutic agent can be mixed in with the polymer. Then the mixture is formed into particles and the solvent is evaporated or driven off, leaving particles like that shown in FIG. 5.

It will be appreciated that the magnetic particles of FIGS. 2-5, or other alternative embodiments, have magnetic properties and carry therapeutic agent. As such, they are capable of being attracted to a target site by a magnetic device and thereby delivering therapeutic agent to the target site.

FIG. 6 shows an alternative structure and placement for a magnetic device in accordance with another embodiment of the invention. FIG. 6 shows the inside of a heart 1 with a magnetic device 60 delivered endocardially, i.e., through the heart. The magnetic device 60 may be delivered to the heart through delivery procedures known in the art.

Similar to magnetic device 10, the magnetic device 60 includes an elongated member 62 and a series of magnetic elements 64. In accordance with an example procedure corresponding to the illustration of FIG. 6, the magnetic device 60 is extended into the desired heart chamber with the magnetic elements 64 placed adjacent the target area 4. Similar to the embodiment of FIG. 1, the magnetic particles 70 delivered through the vasculature are attracted by the magnetic elements 64 to the area of the ischemic tissue 4 which is prone to reperfusion injury. In this way, similar to that described above, the therapeutic agent is delivered in a targeted way to the affected area. In a procedure like that of FIG. 6, the magnetic particles 70 are drawn to the inside layers of the myocardium wall 6, which can often be the area most vulnerable to reperfusion injury.

It will be appreciated that the procedures as described in conjunction with FIGS. 1 and 6 can be performed with variations of the magnetic device for attracting the magnetic particles to the target area. Similarly, such procedures can be performed with magnetic particles as shown in FIGS. 2-5, or other alternative embodiments, with the magnetic particles carrying therapeutic agent and having magnetic material such that they are attracted to the target area by the magnetic device.

In embodiments such as those described above, the therapy is localized by drawing the magnetic particles containing the therapeutic agent to the desired area. A high concentration of therapeutic agent can thus be targeted to the required site, and high systemic levels of the particles and therapeutic agent can be avoided.

While certain embodiments described above are described in the context of heart tissue, magnetic particles as described herein may also be used to target ischemic tissue elsewhere, for example in the brain. In general, similar procedures can be used to deliver the magnetic particles and to attract the magnetic particles to the target site. For use in the brain, the magnetic particles may be sized differently; for example, they may be 100 nm or less to facilitate infusion into the target tissue.

In addition to heart and brain tissue as described above, other target locations are possible. For example, the therapeutic agent may be useful for treating a tumor, e.g., for chemotherapy. Magnetic particles with such therapeutic agent may be provided as described above. A magnetic device as described above may be used for attracting the magnetic particles to the tumor. This system and method may be particularly useful for hard to reach tumors. As another example, the therapeutic agent may be useful for localized neuroprotection. Magnetic particles with such therapeutic agent may be provided as described above. A magnetic device as described above may be used for attracting the magnetic particles to neural cells for neuroprotection, such as to retinal ganglion cells for the prevention of glaucoma progression. Possible therapeutic agents for this purpose may include memantine or another suitable therapeutic agent.

The therapeutic agent used in the present invention may be any pharmaceutically-acceptable agent, particularly those useful in the treatments described above, such as for preventing and/or treating reperfusion injury as discussed above. Other therapeutic agents may also be delivered using magnetic particles as described herein.

Example drugs include anti-proliferative agents or anti-restenosis agents such as paclitaxel, sirolimus (rapamycin), tacrolimus, biolimus, everolimus, and zotarolimus. Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl) ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; structural protein (e.g., collagen) cross-link breakers such as alagebrium (ALT-711); any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A method of delivering therapeutic agent to a target location in a body comprising:
    positioning an angioplasty catheter at an obstruction in a coronary artery for performing an angioplasty procedure, the angioplasty catheter having a perfusion lumen;
    conducting the angioplasty procedure at the obstruction in the coronary artery;
    infusing a plurality of magnetic particles through the perfusion lumen of the angioplasty catheter into the coronary artery upstream from the target location, each magnetic particle carrying a therapeutic agent, wherein the infusing step is performed simultaneously or nearly simultaneously with the angioplasty procedure;
    placing a magnetic device in a position to attract the magnetic particles to the target location, the target location being an area of ischemic myocardium; and
    allowing the magnetic particles to infuse the target location by the attraction of the magnetic particles to the magnetic device.

2. The method of claim 1 wherein the therapeutic agent comprises a therapeutic agent for preventing or treating reperfusion injury.

3. The method of claim 2 wherein the magnetic device is placed through the inside of a heart adjacent inside layers of the myocardium wall to attract the magnetic particles to the ischemic myocardium.

4. The method of claim 2 wherein the magnetic device is placed on the outside of a heart to attract the magnetic particles to the ischemic myocardium.

5. The method of claim 1 wherein each of the magnetic particles of the plurality of magnetic particles comprises a magnetic core and a coating in which the therapeutic agent is contained.

6. The method of claim 1 wherein each of the magnetic particles of the plurality of magnetic particles comprises a core in which the therapeutic agent is contained and a coating comprising magnetic material.

7. The method of claim 1 wherein each of the magnetic particles of the plurality of magnetic particles comprises a porous magnetic material loaded with the therapeutic agent.

8. The method of claim 1 wherein each of the magnetic particles of the plurality of magnetic particles comprises a matrix carrying magnetic material and the therapeutic agent.

9. The method of claim 1 wherein each of the magnetic particles of the plurality of magnetic particles is a nanoparticle having a size of 200 nm or less.

10. The method of claim 1 wherein the therapeutic agent comprises an anti-inflammatory agent, a free radical scavenger, or a vasodilator.

11. The method of claim 1 wherein the infusing step is performed simultaneously with the angioplasty procedure.

12. The method of claim 1 wherein the infusing step is performed nearly simultaneously with the angioplasty procedure.

13. A method of delivering therapeutic agent to a target location in a body comprising:
- providing a plurality of magnetic particles, each magnetic particle carrying a therapeutic agent;
- placing a magnetic device in a position to attract the magnetic particles to a target location; and
- allowing the magnetic particles to infuse the target location by the attraction of the magnetic particles to the magnetic device;
- wherein the therapeutic agent comprises a therapeutic agent for preventing or treating reperfusion injury, and the step of providing the plurality of magnetic particles comprises delivering the plurality of magnetic particles through a blood vessel; and
- wherein the magnetic device is placed on the outside of a heart to attract the magnetic particles to ischemic myocardium.

* * * * *